(12) United States Patent
Spangler

(10) Patent No.: US 11,045,135 B2
(45) Date of Patent: *Jun. 29, 2021

(54) NON-INVASIVE PREDICTION OF RISK FOR SUDDEN CARDIAC DEATH

(71) Applicant: SPANGLER SCIENTIFIC LLC, New York, NY (US)

(72) Inventor: Gregory J. Spangler, New York, NY (US)

(73) Assignee: Spangler Scientific LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/261,248

(22) Filed: Jan. 29, 2019

(65) Prior Publication Data
US 2019/0150769 A1    May 23, 2019

Related U.S. Application Data

(60) Continuation of application No. 15/693,730, filed on Sep. 1, 2017, now Pat. No. 10,226,196, which is a
(Continued)

(51) Int. Cl.
*A61B 5/00* (2006.01)
*G06K 9/00* (2006.01)
(Continued)

(52) U.S. Cl.
CPC .............. *A61B 5/316* (2021.01); *A61B 5/318* (2021.01); *A61B 5/361* (2021.01); *A61B 5/7207* (2013.01); *A61B 5/7246* (2013.01); *A61B 5/7267* (2013.01); *A61B 5/7275* (2013.01); *A61B 5/742* (2013.01); *A61B 5/7405* (2013.01); *A61B 5/7455* (2013.01); *A61B 5/7475* (2013.01);
(Continued)

(58) Field of Classification Search
None
See application file for complete search history.

(56) References Cited

U.S. PATENT DOCUMENTS

| 5,437,285 A | 8/1995 | Verrier et al. |
| 6,217,525 B1 | 4/2001 | Medema et al. |
| (Continued) | | |

FOREIGN PATENT DOCUMENTS

| CN | 202146301 U | 2/2012 |
| EP | 0896282 A1 | 2/1999 |
| WO | 2008007236 A2 | 1/2008 |

OTHER PUBLICATIONS

PCT Search Report dated Nov. 18, 2016.
Bardy. N Engl J Med. Jan. 20, 2005; 352(3):225-37.
Bigger. Circulation 1984; 69:250-8.
Buxton. N Engl J Med 2000; 342:1937-1945.
(Continued)

*Primary Examiner* — Brian T Gedeon
(74) *Attorney, Agent, or Firm* — Botos Churchill IP Law LLP

(57) ABSTRACT

A method and apparatus for the quantitative determination of an individual's risk for sudden cardiac death (SCD) is described. Risk stratification is accomplished (and may have a sensitivity and specificity of greater than about 90%) by determining the presence in any individual being tested for SCD risk of sequences identified herein to correlate quantitatively with SCD risk. Both the number of such sequences present and their alignment scores (similarity) with the SCD risk sequence ensemble are used to calculate quantitative SCD risk.

16 Claims, 9 Drawing Sheets

Related U.S. Application Data division of application No. 15/035,122, filed as application No. PCT/US2014/064577 on Nov. 7, 2014, now Pat. No. 9,775,535.

(60) Provisional application No. 61/901,800, filed on Nov. 8, 2013.

(51) Int. Cl.

| | | |
|---|---|---|
| *A61B 5/316* | (2021.01) | |
| *A61B 5/318* | (2021.01) | |
| *A61B 5/361* | (2021.01) | |
| *G06F 19/00* | (2018.01) | |
| *A61B 5/282* | (2021.01) | |

(52) U.S. Cl.
CPC ........... *G06F 19/00* (2013.01); *G06K 9/0055* (2013.01); *A61B 5/282* (2021.01); *A61B 5/7203* (2013.01); *A61B 5/725* (2013.01); *A61B 2562/221* (2013.01)

(56) References Cited

U.S. PATENT DOCUMENTS

| | | |
|---|---|---|
| 6,443,889 B1 | 9/2002 | Groth et al. |
| 7,123,954 B2 | 10/2006 | Narayan et al. |
| 7,171,269 B1 | 1/2007 | Addison et al. |
| 7,565,194 B2 | 7/2009 | Tan et al. |
| 2003/0100924 A1 | 5/2003 | Foreman et al. |
| 2003/0163057 A1 | 8/2003 | Flick et al. |
| 2005/0004485 A1 | 1/2005 | Crosby et al. |
| 2008/0103403 A1 | 5/2008 | Cohen |
| 2008/0167567 A1 | 7/2008 | Bashour et al. |
| 2008/0262367 A1 | 10/2008 | Mugler et al. |
| 2010/0217144 A1 | 8/2010 | Brian |
| 2012/0179011 A1 | 7/2012 | Moon et al. |
| 2012/0179055 A1 | 7/2012 | Tamil et al. |
| 2013/0046193 A1 | 2/2013 | Guttag et al. |
| 2013/0268013 A1 | 10/2013 | Sanghera et al. |
| 2014/0312692 A1 | 10/2014 | Lin et al. |
| 2015/0216426 A1 | 8/2015 | Burton |

OTHER PUBLICATIONS

Chugh. Nat Rev Cardiol. Jun. 7, 2010(6):318-326.
De Ferrari. J Am Coll Cardiol 2007; 50:2285-90.
EP Search Report issued in corresponding EP application No. 16847122.5 dated Mar. 28, 2019.
Epstein. Heart Rhythm. Jun. 2008; 5(6):934-55.
Ezekowitz. Ann Intern Med. Aug. 2007; 21 ;147(4):251-62.
Gehi. J Am Coll Cardiol 2005; 46:75-82.
Goldberger. circulation. 2008; 118::00-000.
Hohnloser. J Am Coll Cardiol 2003; 41 :2220-4.
Ikeda. J Am Coll Cardiol 2006; 48:2268-74.
International Search Report for PCT/US14/64577 dated Feb. 10, 2015.
Lombardi. Cardiovasc Res (2001) 50 (2): 210-217.
Maggioni. Circulation 1993; 87:312-22.
Moss. N Engl J Med, vol. 346, No. 12.
Myerburg_Circulation 1998; 97:1514-1521.
Pastore Circulation 1999; 99: 1385-94.
PCT Written Opinion issued in corresponding PCT application No. PCT/US16/51460 dated Mar. 13, 2018.
PCT Written Opinion issued in corresponding PCT application No. PCT/US16/51460 dated Nov. 17, 2017.
Pratt. Circulation 1996; 93:519-524.
Rouleau. J Am Coll Cardiol 1996; 27:1119-27.
Salemo-Uriarte. J Am Coll Cardiol 2007; 50: 1896-904.
Simson. Am J Cardiol 1983; 51:105-112.
Verrier, R.L., et al. Microvolt T-wave altemans physiological basis methods of measurement, and clinical utility-consensus guideline by International Society for Holter and Noninvasive Electrocardiology. J Am Coll Cardiol, 2011. 58(13): p. 1309-24.
Zipes, D.P., et al., ACC/AHA/ESC 2006 Guidelines for Management of Patients with Ventricular Arrhythmias and the Prevention of Sudden Cardiac Death—Executive Summary. J AM Col Cardiol, 2006, vol. 48, No. 5, Sep. 5, 2006, p. 247-346.
Bailey, James J, et al., "Utility of Current Risk Stratification Tests for Predicting Major Arrhythmic Events After Myocardial Infarction", Bailey_etal_Utility_of_Current_Risk_Stratification_etc_J_Am_Coll_Cardio_vol. 38_No. 7_2001, Nov. 7, 2001.
Xiaozhong, Chen , et al., "A Novel Methodology for Assessing the Bounded-Input Bounded-Output Instability in QT Interval Dynamics: Application to Clinical ECG With Ventricular Tachycardia", Aug. 11, 2012, pp. 2111-2117.

NON-INVASIVE PREDICTION OF RISK FOR SUDDEN CARDIAC DEATH

CROSS REFERENCE TO RELATED APPLICATIONS

This application is a continuation of U.S. application Ser. No. 15/693,730, filed on Sep. 1, 2017 which is a divisional of U.S. patent application Ser. No. 15/035,122, filed May 6, 2016, U.S. Pat. No. 9,775,535 which is a national phase entry under 35 U.S.C. § 371 of International Application No. PCT/US2014/064577 filed Nov. 7, 2014, published in English, which claims priority from U.S. Provisional Patent Application No. 61/901,800, filed Nov. 8, 2013, all of which are incorporated herein by reference.

FIELD OF THE TECHNOLOGY

The present technology relates to quantitative identification of individuals at risk for sudden cardiac death (SCD) and may involve risk stratification and identification of individuals at risk for SCD. More particularly, the present technology may relate to a noninvasive apparatus, system, device and method, such as using digitized unprocessed data from a standard resting electrocardiogram (ECG), to accurately, rapidly, and easily identify in a quantitative manner individuals at risk for sudden cardiac death with high sensitivity and high specificity.

BACKGROUND OF THE TECHNOLOGY

Sudden cardiac death (SCD) is considered the unexpected death due to cardiac causes of persons with known or unknown cardiac disease, with no underlying cause for death. SCD occurs within a short period of time, for example, generally within one hour, following the onset of symptoms (if any symptoms are encountered).

SCD is a major public health problem as it has reached epidemic proportions, responsible for at least 325,000 deaths per year in the United States alone. (See Goldberger. Circulation. 2008; 118:000-000; Zipes, D. P., et al., *ACC/AHA/ESC* 2006 *Guidelines for Management of Patients With Ventricular Arrhythmias and the Prevention of Sudden Cardiac Death—Executive Summary*. Circulation, 2006: p. CIRCULATION AHA.106.178104). SCD is the second leading cause of death in the U.S., responsible for slightly less deaths than myocardial infarction. Despite decreasing incidence of cardiac deaths secondary to improved medical treatment and percutaneous and surgical revascularization, SCD continues to represent about half of all cardiac deaths. (See Ezekowitz. *Ann Intern Med*. August 2007; 21; 147(4): 251-62).

Most cases of SCD are related to cardiac ventricular arrhythmias (ventricular tachycardia, or VT). Coronary heart disease is associated with the largest number of SCDs. Acute coronary syndrome (ACS) can lead to malignant arrhythmias that are the result of ischemia. Additionally, coronary artery disease (CAD) may lead to microscopic or macroscopic scar formation that can represent substrate for malignant arrhythmias.

Other cardiac diseases, that put patients at increased risk for SCD, include heart failure, cardiomyopathy, left ventricular hypertrophy (LVH), myocarditis, hypertrophic cardiomyopathy, congenital coronary artery anomalies, and myxomatous mitral valve disease. Additionally, the presence of channelopathies such as Brugada syndrome and congenital heart disease or acquired long QT syndrome, idiopathic ventricular fibrillation (VF), Arrhythmogenic Right Ventricular Cardiomyopathy (ARVC), catecholaminergic VT, and Wolff-Parkinson-White (WPW) syndrome increase the risk of SCD.

Implantable cardioverter-defibrillator (ICD) therapy has significantly decreased mortality in high-risk patients, but has done little in terms of affecting overall rates of SCD nationally. (See Bardy. N Engl J Med. 2005 Jan. 20; 352 (3):225-37). This is explained by the fact that two-thirds of patients suffering SCD are in low or intermediate risk groups, resulting in the greatest absolute number of patient deaths (5). However, multiple trials have repeatedly demonstrated that patients in low and intermediate risk groups do not benefit from prophylactic ICDs, demonstrating the lack of sensitivity and specificity of contemporary methods used to stratify SCD risk. The ability to prevent SCD using ICDs is of great importance, as it demonstrates the critical need for a highly sensitive and specific method for identifying individuals at risk for SCD.

Based on the foregoing, the identification of individuals presently considered to be at low or intermediate risk for SCD—but in reality are at high risk—continues to be a major public health concern.

Presently available techniques for the identification of individuals at risk for SCD include clinical history, (e.g., history of congestive heart failure (CHF), decreased left ventricular ejection fraction (LVEF), prior myocardial infarction, Holter monitoring, heart rate variability analysis, signal averaged electrocardiography (SAECG), microvolt T-wave alternans analysis, ambulatory ECG monitoring, metabolic factors and/or parasympathetic tone, heart rate turbulence studies, baroreceptor sensitivity studies and the presence of myocardial scar as detected using magnetic resonance imaging (MRI). Severely reduced LVEF and the presence of advanced CHF (class III or IV) currently serve as the main identifiers for patients at high-risk for SCD and, therefore, for identifying who may benefit from ICD therapy and optimal medical management. (See Epstein. Heart Rhythm. 2008 June; 5(6):934-55; Chugh. Nat Rev Cardiol. 2010 June 7 (6): 318-326, available at http://www.ncbi.nlm-.nih.gov/pmc/articles/PMC3052394/). However, no presently available technique, including those listed above, alone or in combination, has clinically acceptable sensitivity or specificity for the identification of individuals at risk for SCD. Detailed discussion of some exemplary techniques is provided herewith.

Left Ventricular Ejection Fraction AND CLASS III or IV CHF

Left ventricular ejection fraction (LVEF), as evaluated by one of many modalities, and the presence of class III or class IV CHF are the two major predictors of SCD. They are presently the two principle indications used to determine which patients are candidates for ICD placement. [Of course, a history of a prior SCD event is an absolute indication for ICD placement.] (See Epstein. Heart Rhythm. 2008 June; 5(6):934-55; Rouleau. J Am Coll Cardiol 1996; 27:1119-27). Assessment of ejection fraction (EF) has multiple advantages such as accessibility, ease of use, and reproducibility and has been the major determinant of patients who are considered for prophylactic ICD implantation. Several trials have found that an LVEF≤35%, particularly with symptoms of heart failure (CHF), have served as the marker for identifying high-risk patients. (Bardy. N Engl J Med. 2005 Jan. 20; 352(3):225-37). Conversely, multiple studies have found an LVEF≥40% is not an accurate marker for those at increased risk for SCD. This finding suggests that EF may be less useful as a marker for SCD once the EF is greater than 40% on a population basis. (See Ikeda. J AmColl Cardiol 2006; 48:2268-74).

Randomized clinical trials concerning prophylactic ICD implantation have evaluated patients with depressed LVEF. The implications of these studies in the treatment of SCD are limited since most cases of SCD do not occur in patients with low LVEF. (See Zipes, D. P., et al., *ACC/AHA/ESC 2006 Guidelines for Management of Patients With Ventricular Arrhythmias and the Prevention of Sudden Cardiac Death—Executive Summary. Circulation*, 2006: p. CIRCULATION AHA.106.178104). Studies such as multicenter automatic defibrillator implantation trial I (MADIT I), MADIT II and sudden cardiac death in heart failure trial (SCD-HeFT) have all shown significant reductions in arrhythmic and overall mortality with ICD therapy in patients with severely decreased LVEFs. However, the majority of patients who were evaluated, and showed benefit from the prophylactic ICD implantation, had LVEFs≤25%, limiting the ability to extrapolate this data to the low and intermediate risk groups.

Analysis of the multicenter unsustained tachycardia trial (MUSTT) demonstrates that LVEF does not, in fact, represent the greatest risk of total and arrhythmic death. New York Heart Association (NYHA) class, history of heart failure, non-sustained VT, enrollment as inpatient, and atrial fibrillation all portended greater risk as individual markers. Patients with LVEF<30% but with no other risk factors may have a lower predicted mortality risk than patients with LVEF>30% as well as other risk factors. Risk of SCD in patients with cardiomyopathy depends on multiple variables in addition to LVEF and may be further elucidated using other methods. (See Salerno-Uriarte. J Am Coll Cardiol 2007; 50:1896-904). Over all, EF<35% and/or the presence of class III or class IV CHF are important criteria (although present in only a minority of SCD patients) for ICD placement. However, although they are the best presently available methods for SCD risk prediction, they suffer from unacceptably low sensitivity and specificity.

Signal-Averaged Electrocardiogram

In patients with VT, areas of scar may result in slow conduction and prolonged activation of segmental regions of the ventricle. This slowing may manifest itself as ventricular late potentials which are low-amplitude signals that occur after the end of the QRS complex and are thought to reflect slow and fragmented myocardial conduction. (See Simson. Am J Cardiol 1983; 51:105-112). Late potentials have been correlated with abnormal signals found during electrophysiological studies in segmental sections of the endocardium and represent slowly-activated tissue that can represent substrate for reentry. (See Simson. Am J Cardiol 1983; 51:105-112).

Signal averaged electrocardiography (SAECG) is a technique where multiple QRS complexes are digitized, averaged, filtered, and further processed with spectral analysis to facilitate late potential analysis. The sensitivity and specificity of an abnormal SAECG for the prediction of SCD or arrhythmic events has been reported to vary from 30% to 76% and the specificity from 63% to 96% (Bailey. J Am Coll Cardiol 2001; 38:1902-1911). Conversely, the negative predictive value is high, exceeding 95%, also reflecting the low prevalence of SCD.

There are limited data evaluating the prognostic value of SAECG in patients with an LVEF greater than 35% and what data exists has been inconsistent (Ikeda. J AmColl Cardiol).

Microvolt T-Wave Alternans

Microvolt T-wave alternans (MTWA) is a technique that was developed to identify instability of ventricular repolarization during exercise. This instability can lead to dispersion of ventricular refraction, and has been promoted as another methodology for risk stratification for SCD. (See Pastore. Circulation 1999; 99:1385-94; Verrier, R. L., et al., *Microvolt T-wave alternans physiological basis, methods of measurement, and clinical utility—consensus guideline by International Society for Holter and Noninvasive Electrocardiology*. J Am Coll Cardiol, 2011. 58(13): p. 1309-24).

A large meta-analysis has shown prognostic value of a negative MTWA test in post-myocardial infarction (post-MI) patients with reduced ejection fraction, with the strength of the test resulting mainly from a very high negative predictive value (See Gehi. J Am Coll Cardiol 2005; 46:75-82). Additional studies evaluating the prognostic value of MTWA have been inconsistent (See Salerno-Uriarte. J Am Coll Cardiol 2007; 50:1896-904; J Am Coll Cardiol 2007; 50:1896-904).

In a large Italian study, more than 400 patients were tested for MTWA and followed over 18-24 months revealing a negative predictive value of 97%. However, the patients who tested positive for MTWA represented a group who had concomitantly been diagnosed with either non-ischemic cardiomyopathy, NYHA II/III CHF, or a LVEF less than 40%, representing a group of patients already at high risk for SCD and adding little benefit to a low or intermediate risk population. The evidence for usefulness of MTWA in this population is not well-established and has generally been limited by poor positive predictive values due to low prevalence (See Ikeda. J AmColl Cardiol 2006; 48:2268-74).

Ambulatory ECG Monitoring

The detection of ventricular arrhythmias (including premature ventricular contractions (PVCs) and non-sustained ventricular tachycardia (NSVT)) using ambulatory ECG monitoring in patients with left ventricular dysfunction following myocardial infarction is associated with an increased risk for mortality (See Bigger. Circulation 1984; 69:250-8).

However, there is no significant increased value of ambulatory ECG monitoring for risk-stratification in high-risk patients. (See Bardy. N Engl J Med. 2005 Jan. 20; 352(3): 225-37; Moss. N Engl J Med, Vol. 346, No. 12).

Given currently available data, when evaluating the risk of SCD in patients without severe LV systolic dysfunction, the value of ambulatory ECG testing is inconclusive and the low positive predictive value of identifying NSVT in this patient population may limit its clinical utility. (See Maggioni. Circulation 1993; 87:312-22).

Heart Failure

The clinical syndrome of congestive heart failure (CHF) can contribute to arrhythmogenesis in patients with ventricular dysfunction and can increase mortality in patients regardless of LVEF.

Patients with NYHA Class I and II symptoms have been shown to have low overall death rates. However, 67% of total deaths were due to SCD. In contrast, among studies with a mean functional Class IV, there was a high total mortality, but the fraction of SCD was only 29% as the incidence of progressive pump failure increased. (See Goldberger. Circulation. 2008; 118:000-000). This paradox continues to have major implications on the current utility of ICDs in the low and intermediate population.

Heart failure classification is often dynamic in nature depending on the modality at the time, volume status, medications used at the time, and other comorbid conditions that could influence functional status, thereby limiting its utility.

Metabolic Factors

Factors related to ventricular arrhythmias and SCD include serum catecholamine levels and electrolyte imbalances. Manifestations of neurohormonal activation, such as hyponatremia and increased plasma norepinephrine, renin, and natriuretic peptide levels, have been found to be predictive of mortality as well. (See Pratt. Circulation 1996; 93:519-524).

Autonomic Control

Autonomic imbalance has been implicated in SCD, possibly due to reduced vagal tone and sympathetic enhancement, favoring the formation of life-threatening arrhythmias.

Markers of autonomic control, such as heart rate variability (HRV), baroreflex sensitivity (BRS), and heart rate turbulence (HRT), have been found to have independent and in some cases additive prognostic value for SCD. While this effect is more prominent in patients with a reduced ejection fraction, some trials showed significant risk even for patients with relatively preserved EF. (See Lombardi. Cardiovasc Res (2001) 50 (2): 210-217).

Numerous studies have explored the prognostic value of HRV parameters for predicting outcomes in postinfarction patients and have consistently shown depressed HRV is associated with increased mortality. (See Lombardi. Cardiovasc Res (2001) 50 (2): 210-217). However, data regarding the prognostic significance of HRV for predicting SCD in patients with ischemic heart disease is lacking, and serves no role in risk-stratification. All data to date concerning autonomic control in patients with a relatively preserved LVEF has not proven significant. (See De Ferrari. J Am Coll Cardiol 2007; 50:2285-90).

Based on the foregoing, at present there are no methods with acceptable sensitivity or specificity to be clinically useful in the identification of people at risk for SCD. There is a critical need for a device able to identify individuals at risk for SCD (independent of any underlying pathology) with high sensitivity and specificity. This is particularly true because there are presently available technologies able to prevent SCD in individuals at risk (e.g., ICDs). There is also a great need to accurately identify patients in currently recognized high-risk groups for SCD who would not benefit (and possibly suffer) from high-cost ICD placement.

Point of convention: In the literature, the term Sudden Cardiac Death (SCD) refers to 1) the occurrence of those ventricular arrhythmias which, if not immediately and successfully treated (e.g., by an external or implantable cardioverter-defibrillator) lead to death or 2) the death of an individual from such a ventricular arrhythmia. In contrast, some authors refer to the occurrence of these most often lethal ventricular arrhythmias as Sudden Cardiac Arrest (SCA), and use the term SCD specifically in those cases in which the arrhythmic event results in death. Throughout the remainder of this specification, the first and more commonly used convention is intended.

BRIEF SUMMARY OF THE TECHNOLOGY

The present technology relates to a non-invasive risk stratification methodology for predicting an individual's risk for SCD.

A first aspect of the present technology relates to a method for determining electrocardiogram (ECG) sequences (e.g., continuous, adjacent segments [in time] of digital ECG voltages) specifically indicative of a risk for sudden cardiac death (SCD). The method may include receiving a first plurality of ECG measurements, e.g., digital measurements, taken from individuals who have no history of heart disease and no history of SCD, receiving a second plurality of ECG measurements, e.g., digital measurements, taken from individuals who have a history of heart disease (such as representing a variety of etiologies, including ischemic heart disease, cardiomyopathies, congestive heart failure, etc.) but no history of SCD, and receiving a third plurality of ECG measurements, e.g., digital measurements, taken from individuals who have a history of SCD (with or without a prior history of heart disease). One or more processor(s) may identify those ECG sequences unique to the third plurality of ECG measurements, but not those sequences obtained from normal or non-SCD heart disease individuals. The identified ECG sequences are present in the third plurality of ECG measurements but absent from the first and second pluralities of ECG measurements. The processor, after isolating digital ECG sequences from any standard resting ECG machine, may determine the ECG sequences indicative of the risk for SCD based on the identified ECG sequences. Each ECG measurement may be obtained from a standard resting 12-lead ECG machine.

In some cases, the method may include preprocessing, with a preprocessor, such as a processor that extracts digital ECG data from standard ECG machines. The preprocessor may then filter the digital ECG data to remove noise contaminating the data. In addition, it may construct or compute the first and second derivatives of the filtered data for additional risk sequence extraction/isolation. The digital ECG measurement may be denoised by at least one of the following methods: digital filtering and a combination of wavelet denoising methods. The noise may arise from all of the following sources: electrical noise, mechanical noise, respiration, white noise, movement artifact, and baseline drift. In some cases, the first and second derivatives calculated from this data are generated.

The processor may identify and isolates those digital sequences unique to individuals who have experienced SCD In some cases, the processor may identify and isolate those ECG sequences unique to the third plurality of ECG measurements by 'subtracting' (such as by methods discussed herein) from the complete ECG sequences present in patients who have experienced SCD (or SCA, as described above) all of the digital ECG sequences present in individuals with or without heart disease that have not experience SCD. The processor may identify and isolate those ECG sequences relatively unique to the third plurality of ECG measurements (sequences). This is accomplished by analyzing all of the digital ECG sequences present in the third pluralities of ECG measurements; aligning these ECG sequences with respect to all of the ECG sequences present in the first and second plurality of ECG measurements, and calculating an alignment score (or equivalently, similarity score) for all of the sequences of the third plurality to the combined sequences of the first and second plurality. All sequences of the third plurality with low alignment or similarity scores to the combined sequences of the first and second plurality groups are then isolated. These identified and isolated sequences are then defined as putative SCD-specific risk sequences.

Further analyses of these putative risk sequences may be performed by one or more processors in order to determine the actual SCD risk sequences and the optimal combination/collection of risk sequences to use in order to determine patient risk for SCD. The processor performs these operations using a plurality of local and global optimization methods. This is using a separate set of digital ECG sequences representative but unique from the above patient groups (pluralities). In particular, the processes of optimization are done with data not used in the identification and isolation of putative SCD risk sequences.

A beneficial application of the present technology is a method, such as in a processor or other processing apparatus, for determining an individual's risk for sudden cardiac death (SCD), such as with high sensitivity and specificity (e.g., greater than about 90%). The method may include extracting (directly or wirelessly) digital ECG data from any individual being tested using any standard ECG device, and determining the number and accuracy of alignment (alignment or similarity score) of the ECG sequence present in the patient undergoing SCD risk analysis with the optimal SCD risk sequence ensemble previously constructed (as described above). Determining the number of SCD risk sequences and the accuracy of alignment (similarity) of these sequences with members of the optimized SCD risk sequence ensemble, SCD risk is determined quantitatively with high sensitivity and specificity (e.g., greater than 90%).

The foregoing summary is illustrative only and is not intended to be in any way limiting. In addition to the illustrative aspects, embodiments, and features, described above, further aspects, embodiments, and features will become apparent by reference to the drawings and the following detailed description.

BRIEF DESCRIPTION OF THE DRAWINGS

The present technology is illustrated by way of example, and not by way of limitation, in the figures of the accompanying drawings, in which like reference numerals refer to similar elements including.

DETAILED DESCRIPTION

Figure 1:
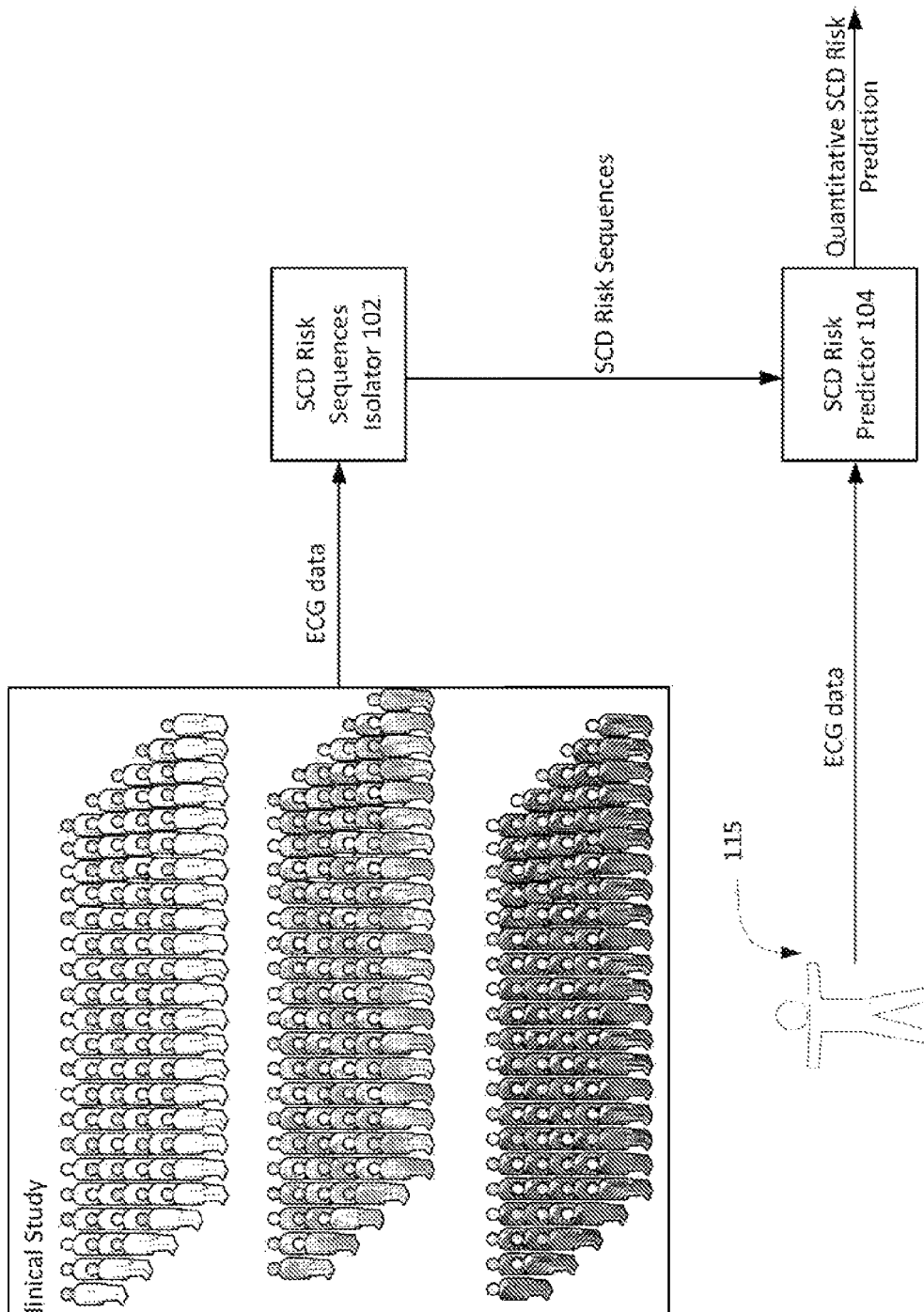
FIG. 1 is an illustrative overview of the present technology including an SCD risk sequences isolator and an SCD risk predictor.

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description provides specific details of aspects of the technologies detailed herein. The headings and subheadings provided herein are for convenience and ease of reading only.

1. Overview

The present technology described herein generally relates to quantitatively identifying individuals at risk for Sudden Cardiac Death (SCD), which may also be termed Sudden Cardiac Arrest (SCA), using noninvasive methods. Such noninvasive mechanisms include identifying and isolating digital electrocardiogram (ECG) subsequences, which may be understood herein as measured cardiac related biopotential signals not strictly requiring a 12-lead ECG, which correlate with the occurrence of lethal ventricular arrhythmias or SCD based on information obtained from clinical studies. The digital ECG subsequences identified as such may be referred hereinafter as SCD risk sequences.

Specifically, to identify the SCD risk sequences, the noninvasive mechanisms discussed herein analyze digital ECG data from survivors of SCD, as well as individuals with and without heart disease who have not experienced SCD. A survivor of SCD may be defined as an individual who has experienced a deadly ventricular arrhythmia or SCD (or SCA), but has survived the event as a result of cardioversion. Examples of cardioversion may include applying an electrical shock to an individual via an external cardiac defibrillator or an implanted cardioverter defibrillator (ICD).

The digital ECG data may, for example, be obtained from a standard ECG machine, such as a standard resting 12-lead ECG machine. Once the digital ECG data is obtained, the noninvasive mechanisms may identify and isolate SCD risk sequences from the digital ECG data.

The optimal collection of SCD risk sequences used for quantitative risk prediction is constructed by the processor through the use of a variety of local and global optimization techniques.

The noninvasive mechanisms discussed herein also predict an individual's quantitative risk for SCD using the optimal set of SCD risk sequences. For instance, the present technology may detect the presence of the SCD risk sequences in an individual's ECG. Based on the quantitative presence or absence of SCD risk sequences in the individual's digital ECG data, the present technology may calculate the individual's risk for SCD and output a scalar number that reflects the individual's quantitative risk for SCD. The quantitation is performed based upon the number of risk sequences identified in the ECG data derived from the individual being tested, as well as the alignment score (similarity) of the patient ECG data to the SCD risk sequences.

By way of illustration, FIG. 1 shows an example operating environment of the present technology. The present technology may include two distinct apparatuses—(1) an SCD risk sequences isolator 102 and (2) an SCD risk predictor 104. The SCD risk sequences isolator 102 may identify and isolate, from clinical studies, SCD risk sequences present in survivors of SCD which correlate with the occurrence of lethal ventricular arrhythmias or SCD. The optimal collection of risk sequences is created from the putative SCD risk sequences by the risk sequence isolator using local and global optimization methods.

For instance, the predictor 104 may be implemented in an individual apparatus, e.g., an ECG device, a general monitoring device, a Holter-type recording device, a PC chip, an ICD, or ATP-ICD (antitachycardia pacing ICD), SCD ablation equipment, etc. or as a self-contained unit.

The isolator 102 may identify, isolate, and optimally group the SCD risk sequences, such as in the form of data representing those sequences. The isolator 102 may require as input (e.g., digital ECG data) collected from individuals (such as a clinical study) in order to identify and isolate the SCD risk sequences—those digital ECG sequences that correlate with the occurrence of SCD. Once identified and isolated in such a training process, these sequences are further optimized into a collection of risk sequences. This optimized collection of SCD risk sequences may be programmed into the memory of the SCD risk predictor 104. It is therefore apparent that the isolator 102 may be employed once for the identification, isolation, and construction of the optimal collection (using local and global optimization techniques) of SCD risk sequences derived from clinical study.

Figure 2:
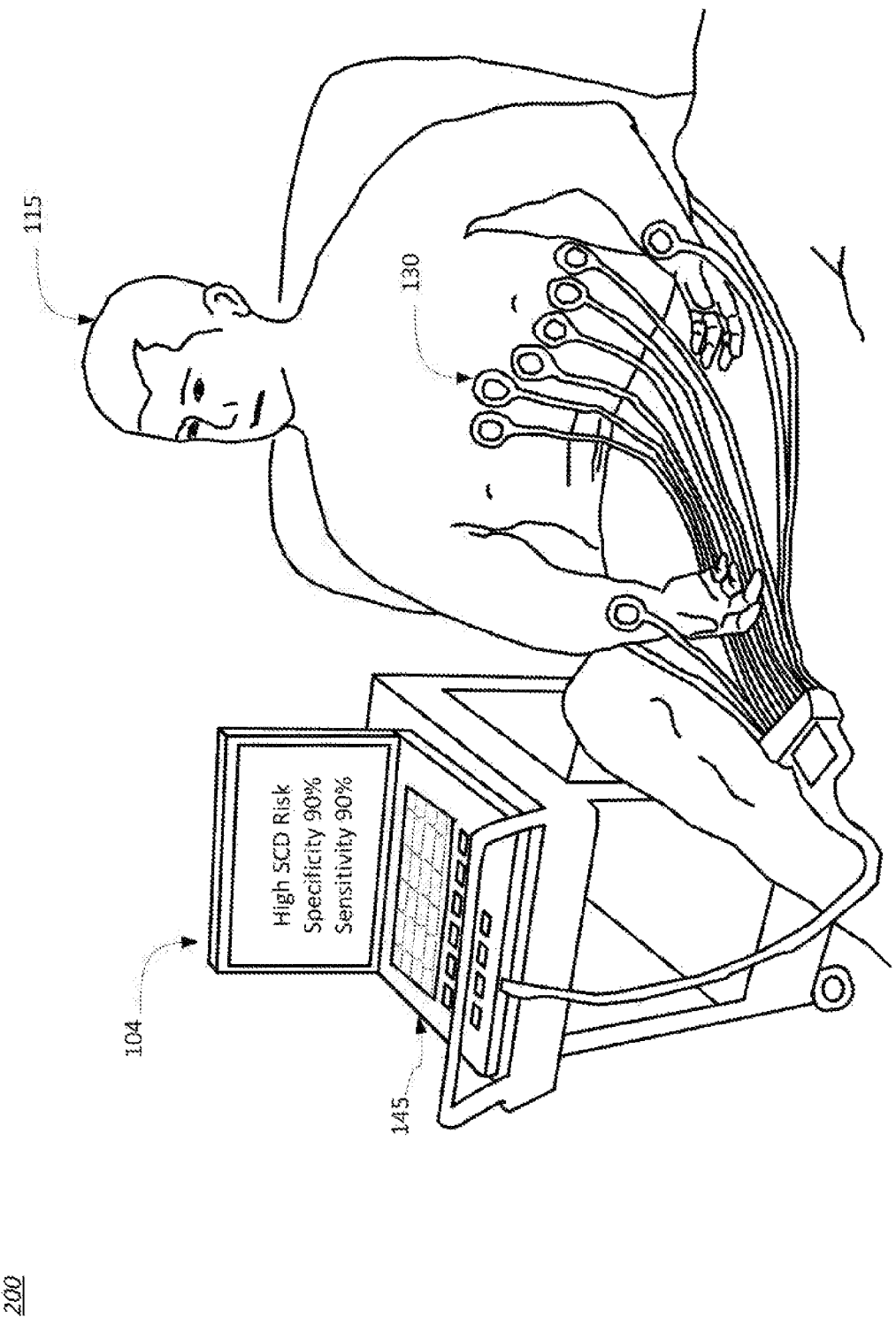
FIG. 2 shows an example clinical application of the SCD risk predictor of FIG. 1 in accordance with the present technology.

The SCD risk predictor 104 may be then preprogrammed with those sequences identified by one or more clinical studies. The predictor 104 may then predict an individual's SCD risk level by searching for the presence of these SCD risk sequences in an individual's measured digital ECG data. Quantitative risk prediction is performed by determining the number of risk sequences present in the test patient, as well as the accuracy of alignment (similarity) of the sequences in the rest patient to the risk sequences in the optimized risk sequence ensemble. In some examples, the predictor 104 may be used once or on multiple occasions in any given individual or many different individuals. Thus, the preprogrammed risk predictor 104 can be a tool in clinical practice. For instance, as illustrated in FIG. 2, the predictor 104 may operate in concert with a standard ECG device 145 measures the digital ECG data of an individual 115 via electrodes 130. The predictor 104 may predict the individual's risk for SCD and display on a screen the predicted level of the risk for SCD, along with accuracy measures (e.g., specificity and sensitivity) of such predictions.

Figure 3:
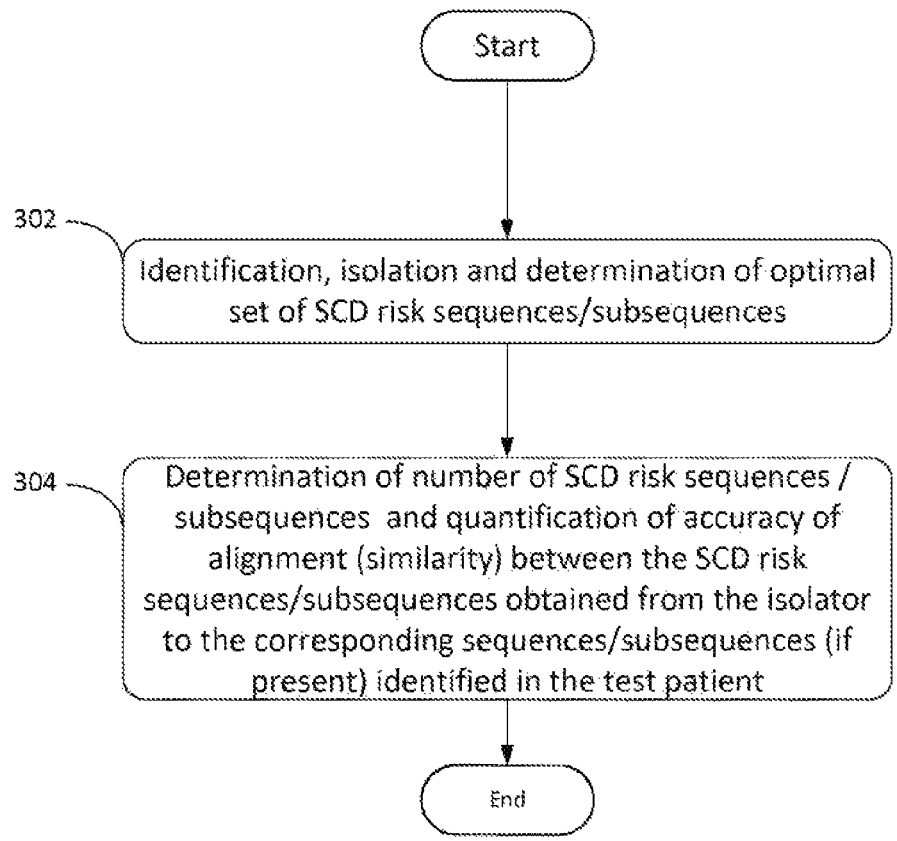
FIG. 3 illustrates a flow chart of an overall process performed by the SCD risk sequences isolator and the SCD risk predictor in accordance with the present technology.

FIG. 3 is a flowchart that illustrates an embodiment of a method of operation of the present technology. Methods illustrated in the flow chart of FIG. 3 and other flowcharts discussed herein may be executed by processors. In some examples, methods illustrated in each flow chart may be carried out periodically, continuously, as needed, as triggered, or in another manner. Each method may include one or more operations, functions, or actions as illustrated by one or more of the blocks. A block may represent a process of information, a transmission of information, or a combination thereof.

In a flowchart, although the blocks are illustrated in a sequential order, these blocks may also function in parallel or in a different order than those described herein, depending on the functionalities involved. Also, the various blocks may be combined into fewer blocks, divided into additional blocks, sub-blocks, or omitted based upon the desired implementation. Furthermore, blocks illustrated in various flow charts may be combined with one another, in part or in whole, based on the functionalities involved.

Referring to FIG. 3, at block 302, the isolator 102 may identify, isolate, and optimally group SCD risk sequences from digital ECG sequences unique to survivors of SCD (SCA). The SCD risk sequences may represent sequences that are responsible for the occurrence of SCD. At block 304, the predictor 104 may determine any individual's risk for SCD, where the individual may or may not be a survivor of SCD. The predictor 104 may obtain the individual's digital ECG measurement from any ECG device 145 as illustrated in FIG. 2. The predictor 104 may search for the presence of SCD risk sequences with respect to the individual's ECG measurement, an determine the accuracy of alignment (similarity) between the patient's identified risk sequences and those used to preprogram the isolator.

More details regarding implementation of the isolator 102 and the predictor 104 are provided herewith.

2. SCD Risk Sequence Isolator 2.1 General Operation of the Isolator

As described earlier, the processes of the isolator 102 may include the identification or isolation of sequences that correlate with the occurrence of SCD. This may be performed in several steps.

Unprocessed digital ECG data can be obtained either directly from one or more ECG leads, or from any ECG-capable device prior to processing of the input data. This is the desired format of data used by both the isolator and the predictor. At a first step, the isolator may evaluate input (e.g., digital ECG data) obtained in a clinical study. This data may include standard, resting 12-lead digital ECG data obtained from a number of groups of individuals (e.g., three groups of individuals) such as the following:

1. one group of individuals with no history of heart disease and no known risk factors for SCD;
2. one group of individuals with heart disease (of a variety of etiologies), but no history of SCD, and
3. one group of individuals with or without a history of heart disease that have experienced SCD (SCA).

All 12 leads of digital ECG data from each person in the study/studies may be used as input for the isolator 102. This digital data is obtained by the isolator either directly from the ECG leads, or from the ECG machine prior to any preprocessing or processing. In either case, lead placement is not modified for the study from usual ECG lead placement. The isolator preprocessor can operate upon 12 digital ECG signals (one corresponding to each ECG lead) from each individual in the clinical study/studies.

At a second step, the digital ECG data obtained from each patient and stored in the isolator 102 memory can be denoised by its preprocessor. Complete systematic denoising is required for all digital ECG data. The preprocessor may perform denoising first by employing digital filter techniques. Finite Impulse Response (FIR) filter techniques may be used to optimally perform this initial denoising function. Denoising may then be optimized using wavelet packet techniques. This extensive degree of denoising is required to obtain digital ECG data with a very high signal-to-noise (STN) ratio (minimal loss of significant ECG information and maximal removal of noise resulting from a variety of sources).

At a third step, for the purpose of enabling additional higher-level digital ECG sequence analysis, the preprocessor may compute the first and second derivatives of the optimally denoised digital data. Analysis of data corresponding to the first and second derivative of the digital input data is beneficial since it correlates with critical electrical activities (e.g., depolarization and repolarization, conduction velocity, and conduction turbulence) within the heart. Thus, the transformed data may provide additional sources of potential SCD risk sequences.

Subsequently, all of the fully preprocessed digital ECG data (as well as the first and second derivatives of this data) may then be further processed by the processor(s) within the SCD risk sequence isolator 102.

The identification and isolation of the SCD risk sequence may then be performed by the isolator 102 such as in a processing unit.

In such a processing unit, the preprocessed ECG data obtained and derived from those individuals in the study(ies) who have experienced SCD are completely analyzed. In particular, using alignment techniques, all of the digital ECG sequences present in the groups of patients (with or without a history of heart disease) who have not experienced SCD (SCA) are removed from the collection of ECG sequences present in one or more patients comprising the group of patients who have experienced SCD (SCA). The actual method used to identify, isolate, and construct the optimal collection of SCD risk sequences (and subsequently used to train the SCD risk predictor) requires three steps:

1) In a sequential manner, every single mathematically possible alignment between every possible length (of adjacent ECG data points) of denoised digital ECG serially beginning at every time point in the ECG data collection obtained and/or constructed from every patient in the study(ies) is abstractly created. The quality of alignment (similarity) of each of these ECG data pairings between the corresponding ECG leads of all patients in the study(ies) (as well as the derivatives of this data) is quantitated determined using a variant of the root mean square (RMS) error method. Determination of those alignments with alignment values above or below certain thresholds allows the identification of ECG segments relatively common to and relatively unique to patient groups. This information allows the identification and isolation of sequences relatively unique to patients (with or without heart disease) who have experienced SCD (SCA). This collection of sequences is relatively free of sequences present in patients with any of a variety of heart diseases who have not experienced SCD. These sequences are referred to as 'putative SCD risk sequences'.

2) Using published values of SCD (SCA) incidence (as a function of time) in individuals with no history of heart disease and patients with heart disease of a variety of types (i.e., ischemic heart disease, congestive heart failure, etc.) with or without a prior SCD event (SCA), the time dependent risk of every patient in the study for SCD is calculated. Using local optimization methods, the putative SCD risk sequences which optimally correlate with the detailed patient data are identified and isolated. These sequences are referred to as SCD risk sequences (as opposed to putative SCD risk sequences).

3) The collection of SCD risk sequences which best correlate with the above patient and patient group information and data is then constructed using global optimization techniques. The optimized collection of SCD risk sequences contains sequences from each ECG lead as well as the sequences obtained by first and second order differentiation of the input ECG data.

Figure 5:
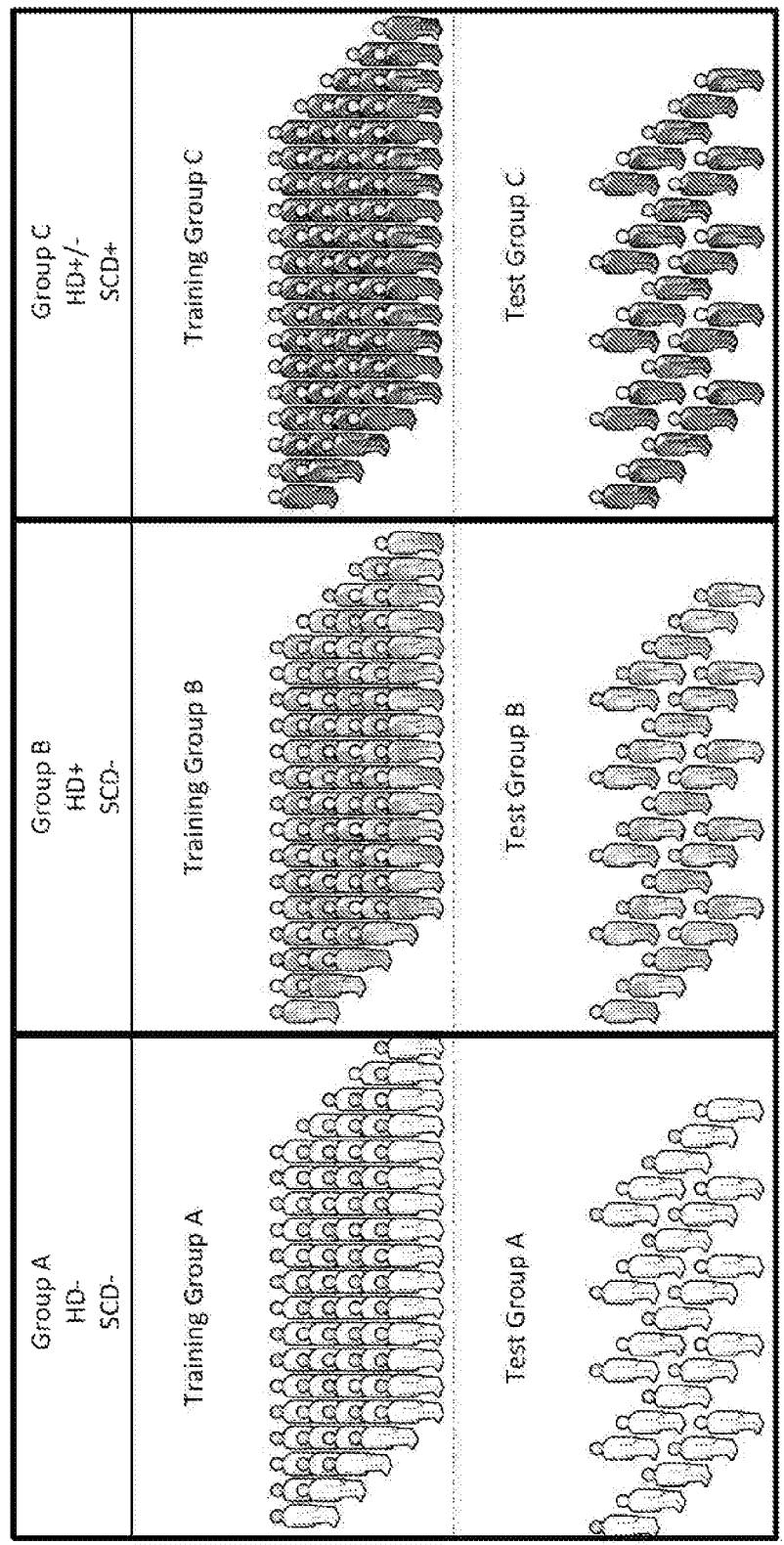
FIG. 5 illustrates the clinical groups used to obtain the clinical data for the construction of the optimized SCD risk sequence ensemble as well as the data to calculate the sensitivity and specificity of the SCD risk predictor.

The sensitivity and specificity of the SCD risk predictor trained by the optimized SCD risk sequence group or ensemble constructed in any given clinical trial (the ensemble being constructed from the SCD risk sequences identified and isolated in the clinical trial by the preprocessor followed by global optimization technologies, as described previously) is determined using a separate group of patient—the test patients—from the clinical trial. As demonstrated in FIG. 5, these test patients consist of: individuals with no history of heart disease who have never experiences SCD, individuals with a history of heart disease who have never experiences SCD, and individuals (with or without a history of heart disease) who have survived SCD (SCA). It is important to note that the test groups of individuals used to determine the sensitivity and specificity of the SCD risk predictor have never been previously seen or used by the SCD risk predictor. In this manner, the sensitivity and specificity of the SCD risk predictor are determined to be greater than 90%. These values have been obtained in two separate clinical trials.

2.2 Example Components of Isolator

Figure 4:
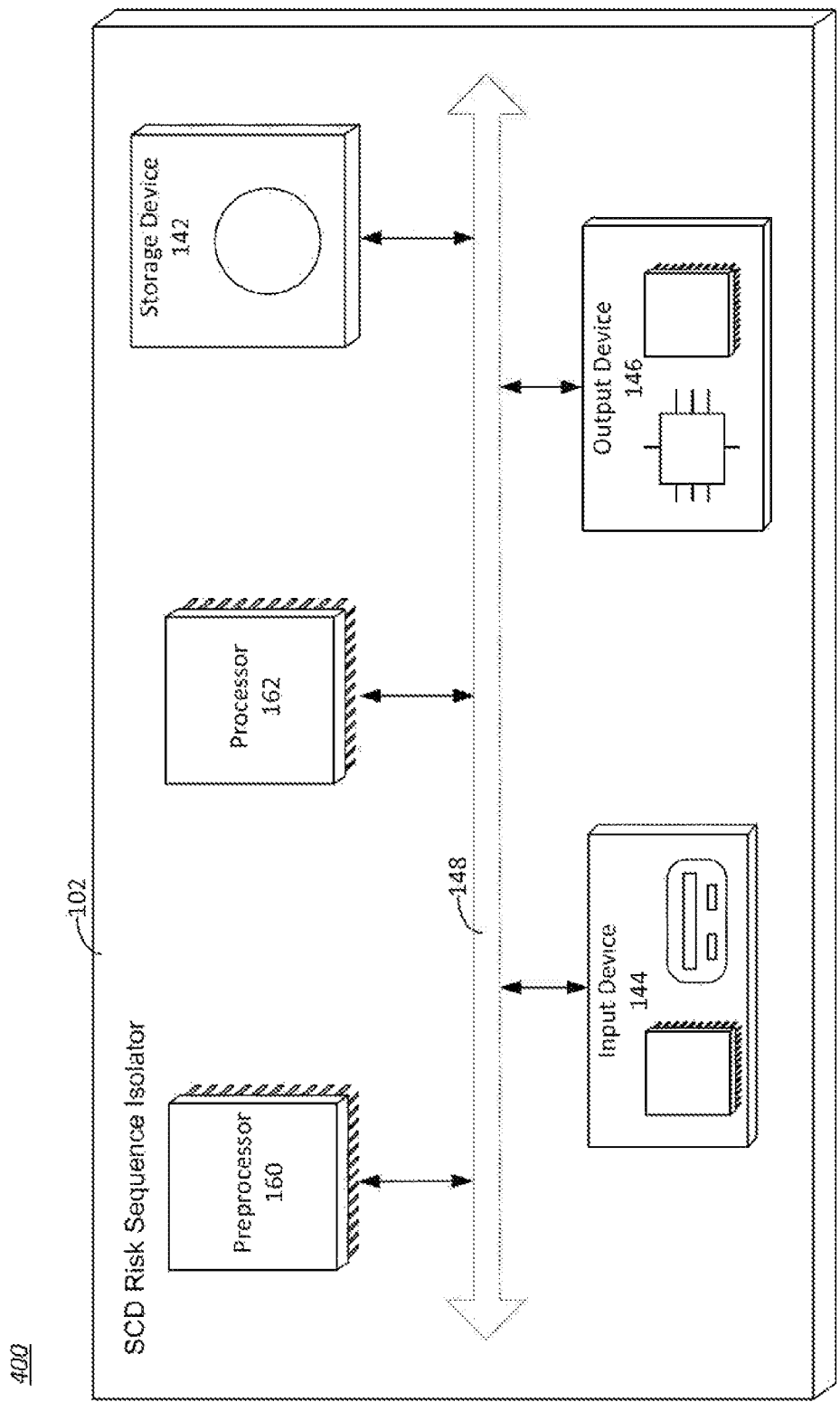
FIG. 4 shows a component diagram of the SCD risk sequences isolator.

FIG. 4 is a schematic diagram of an example implementation of the isolator 102. As illustrated, the isolator 102 may include one or more of the following components: one or more preprocessors such as preprocessor 160, one or more processors 162, a storage device 142, an input device 144, and an output device 146. Components of the isolator 102 may be communicatively coupled together in either a wired or wireless fashion. In some cases, the methodologies of the processing components may be achieved in a single processor or multiple processors. In one example as illustrated in FIG. 4, the components may be coupled together by a system bus 148. Detailed description of each component is as follows.

2.2.1 Preprocessor and Processor of Isolator

The preprocessor 160 and processor 162 may control the functions of the isolator 102. For instance, the preprocessor 160 may perform the following functions, including denoising and the calculation the first and second order derivatives of the digital input data. The processor 162 may perform the following operations, including putative SCD risk sequence identification and isolation, SCD risk sequence identification and isolation, and construction of the optimal ensemble of SCD risk sequences. The preprocessor 160 and processor 162 may be of any type including but not limited to a general purpose preprocessor or processor and a special purpose or dedicated preprocessor or processor, e.g., an application-specific integrated circuit (ASIC), a digital signal processor (DSP), a graphical processing unit (GPU), a floating point processing unit (FPU), and the like. The processor 162 may refer to a single processor, or a collection of processors of the same type or various types, which may or may not operate in a parallel-processing mode.

The processor 162 may communicate with other components of the isolator 102. In one example, the processor 162 may execute computer-readable instructions or other instructions stored in the storage device 142. The processor 162 may read and write the data during execution of the computer-readable instructions. In another example, the processor 162 may act upon input signals provided by the input device 144.

2.2.2 Storage Device of Isolator

The storage device 142 may provide storage for the isolator 102 by using one or more non-transitory computer-readable media. The computer-readable media may store volatile data, non-volatile data, or a combination thereof. Some computer-readable media may store data for a short period of time. Other computer-readable media may store data persistently for a long period of time.

The computer-readable media may include primary storage, secondary storage, or a combination thereof. The primary storage may be simply referred to as memory, which is directly accessed by the processor 162. The secondary storage may be indirectly accessed by the processor 162 via the primary storage.

The computer-readable media may be of different types including random-access memory (e.g., SRAM and DRAM), read-only memory (e.g., Mask ROM, PROM, EPROM, and EEPROM), non-volatile random-access memory (e.g. flash memory), a magnetic storage medium, an optical disc, a memory card, a Zip drive, a register memory, a processor cache, a solid state drive (SSD), and a redundant array of independent disks (RAID), among other possibilities.

The storage device 142 may store one or more computer-readable instructions, data, applications, processes, threads of applications, program modules and/or software, which are accessible or executable by the processor 162 to perform at least part of the herein-described methods and techniques.

By way of example, the computer-readable instructions in the storage device 142 of the isolator 102 may include logic that identifies and isolates SCD risk sequences.

Examples of data stored in the storage device 142 may include but not limited to variables, results, data obtained from one or more ECG devices, the SCD risk sequences, and parameters used to identify the SCD risk sequences, among other possibilities.

2.2.3 Input Device

The input device 144 may refer to one or more peripheral devices configured to receive information from individuals. The input device 144 may communicate such information to other components of the isolator 102.

By way of example, the input device 144 may be one or more ECG leads, an ECG device, such as a standard resting 12-lead ECG device or device with more or fewer of such electrode leads. The input device 144 may also include user input components such as a keyboard, keypad, touch pad, point device, track ball, joystick, voice recognition device, touch-sensitive surface, microphone, digital camera, mouse, buttons, switch, scroll-wheel, scanner, GPS receiver, movement sensor, location sensor, infrared sensor, optical sensor, Radio Frequency identification (RFID) system, and wireless sensor, among others. In some examples, the input device 144 may include an external defibrillator or implantable cardioverter-defibrillator (ICD or ATP-ICD).

The input device 144 may provide a number of different types of digital input data, such as a digital ECG measurement, an electrogram (EGM) measurement, audio data from a microphone, text data from a keypad, video or image data from a camera, and gesture data from a touchpad, just to name a few. This data may be gathered from clinical studies on groups of individuals such as with other devices and transferred in digital form to the isolator via the input. This input is used by the isolator for its identification and isolation of SCD risk sequences.

2.2.4 Output Device of Isolator

The output device 146 may communicate one or more outputs of the isolator 102 to the SCD risk predictor 104.

The output device 146 may include output components such as a digital output file, a digital output storage device, a visual display, audio transducer, light indicator, tactile transducer, printer, light bulb, and vibration generator, among others. The output device 146 may provide a number of different types of output data, such as digital data, visual output via a display, audio output via a speaker, and tactile output via a vibration generator, among others.

By way of example, the output device 146 may be a quantitative SCD risk predictor. Also, the output device may be a digital storage device. In some examples, the output device 146 may include one or more audio transducers in the following forms: a speaker, headset, jack, earphone, and audio output port.

2.3 Example Logic and Methods of Isolator

The isolator 102 may include computer algorithms such as computer-readable instructions, ASICs, FPGAs, DSPs, integrated circuits, modules, firmware, or a combination thereof, among other possibilities. These computer algorithms may be implemented in a signal bearing non-transitory computer-readable storage medium in a variety of forms. The isolator 102 may perform several functions, including identifying, isolating, and/or quantification of SCD risk sequences from patient data obtained from survivors of SCD (in concert with digital ECG data from patients who either have or do not have heart disease but have never experienced SCD). The isolator 102 may perform only once or be reused several times (upon digital ECG data from patients of different clinical studies). The SCD risk sequences identified and isolated by the isolator 102 may be transferred and stored by a storage device or by the predictor 104.

The SCD risk sequence isolator 102 may generally identify, isolate, and optimally group and organize SCD risk sequences into ensembles. These SCD risk sequence ensembles may be used to train any of a variety of SCD risk predictors.

According to some aspects of the present technology, the isolator 102 may be a one-time-only process, that is, the isolator 102 may be used only once to identify, isolate and optimally group the SCD risk sequences that are present in those individuals of a particular clinical study. These sequences serve as a standard for future risk predictions by the predictor 104. The isolator 102 may also be reused to identify, isolate and optimally group SCD risk sequences present in the individuals of a different clinical groups or studies. The isolated SCD risk sequences obtained by the isolator 102 in any given clinical study may be stored in the isolator, on a disc, or used to preprogram any given predictor 104.

Figure 6:
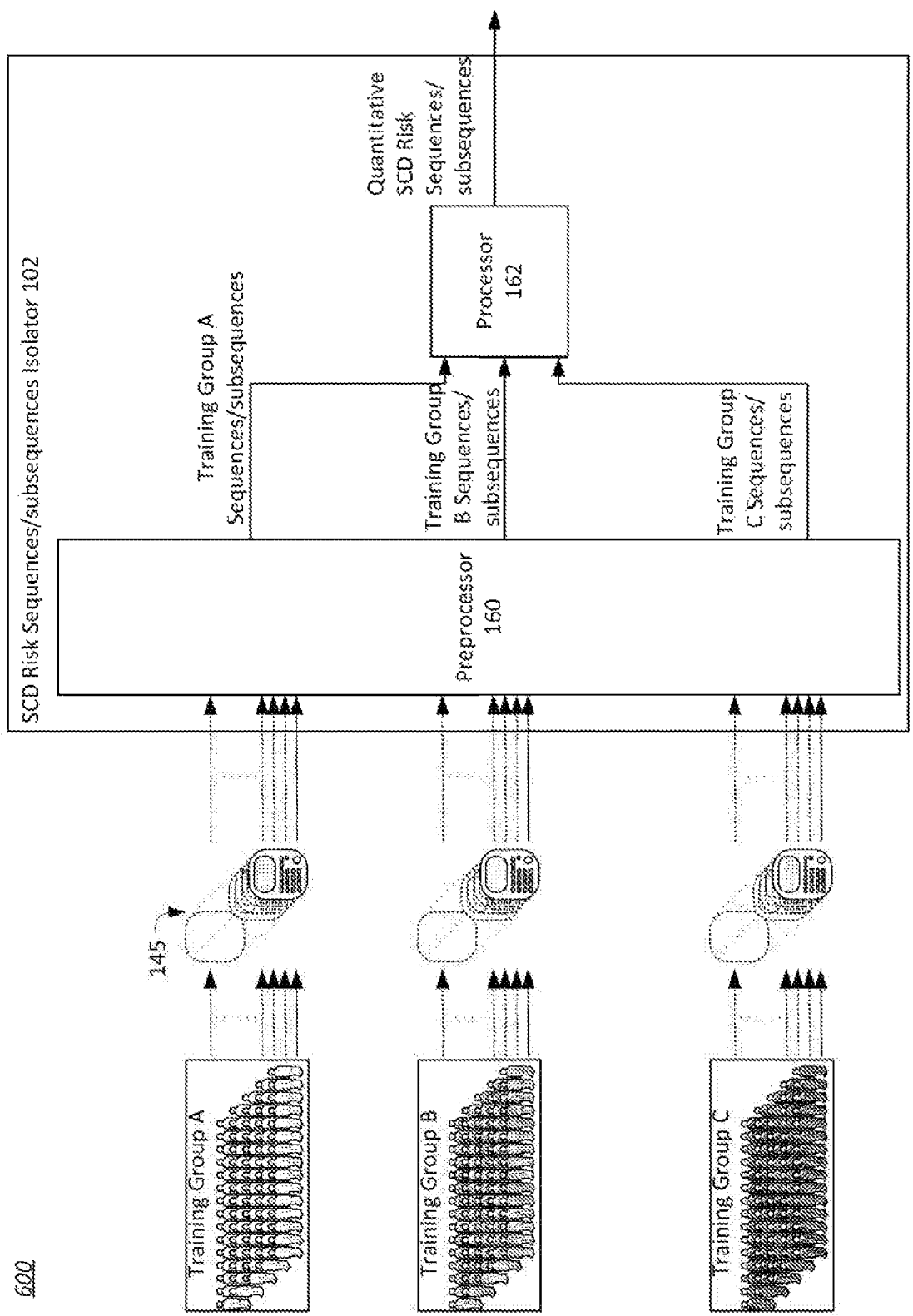
FIG. 6 is a block diagram of an example implementation of the SCD risk sequences isolator.

FIG. 6 illustrates an exemplary configuration of the isolator 102. As illustrated, the isolator 102 may include one or more of the following units: a preprocessor 160 for ECG data denoising and data derivative calculations, and a processor 162 for identifying, isolating and optimally grouping the SCD risk sequences. Detailed description of each unit is as follows.

2.3.1 Isolator Preprocessor

Figure 7:
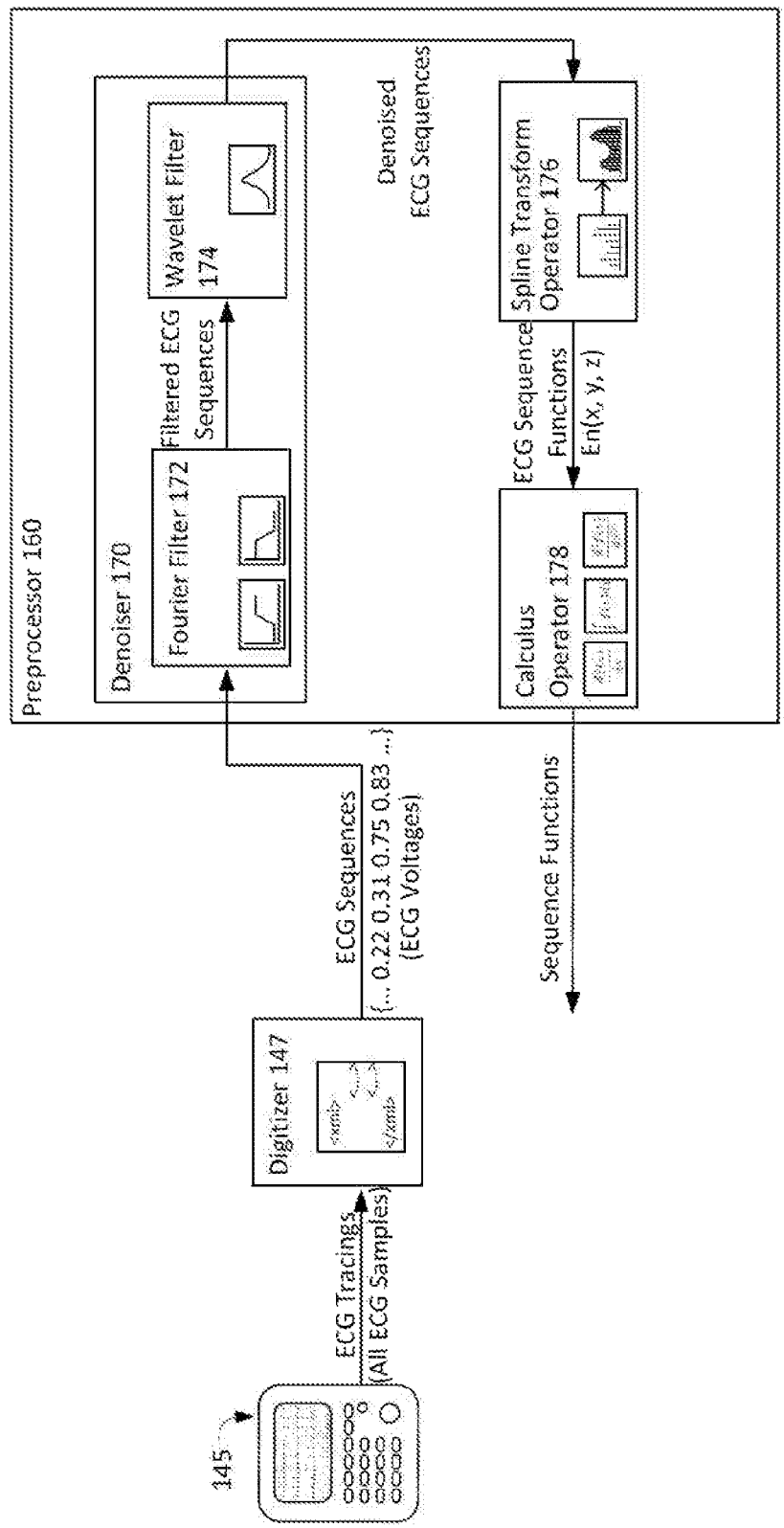
FIG. 7 is a block diagram of the preprocessor of the SCD risk sequences isolator.

FIG. 7 is a schematic illustration of an exemplary configuration of the isolator preprocessor 160. The isolator preprocessor 160 may preprocess digital ECG measurements, such as those obtained from the clinical study/studies described above. The digital ECG measurements may include all of the digital information obtained from all leads of any digital ECG's device or from the ECG lead itself. As illustrated in FIG. 7, the digital ECG measurements of any human subject in the clinical study/studies may be obtained from an ECG device 145. The digital ECG device 145 may be a standard resting 12-lead digital ECG device or such a measurement device of any other number of leads. Alternatively, the digital ECG device 145 may be a management system, such as the MUSE Cardiology Information System by GE Healthcare, which stores and manages digital ECG measurements output by one or more digital ECG devices. The digital ECG measurement obtained from an individual may include measured voltages obtained from each lead. For instance, as illustrated in FIG. 7, the digital ECG measurement extracted from a standard resting 12-lead digital ECG device for one individual may have twelve sequences representing digital 12-lead ECG measurements obtained from the individual. A sequence may represent the voltage measures as a function of time associated with one of the twelve leads: Lead I, Lead II, Lead III, Lead aVR, Lead aVL, Lead aVF, Lead V1, Lead V2, Lead V3, Lead V4, Lead V5, and Lead V6. For example, each individual in the Training Groups A, B, and C may have twelve sequences. Different individuals may have different or similar sequences associated with each lead. Each digital ECG measurement may include measurements taken from a period of time (e.g., approximately 10 seconds, or other suitable time periods).

As illustrated in FIG. 7, the preprocessor 160 may include one or both of the following subunits: a denoising subunit 170, and a computational subunit which calculates the first and second derivitives of the denoised input data.

The denoising subunit 170 may receive digital ECG measurements, and remove signal noise using a Finite Impulse Response (FIR) digital filter. The signal noise may include electrical noise, mechanical noise, respiration-related noise, white noise, movement artifact, and baseline drift.

Wavelet packet filtering may then performed by the isolator preprocessor 160 for further signal denoising. The wavelet filters 174 may use several wavelet families at a variety of decomposition levels to further denoise the signals. The wavelet filter 174 may employ entropy methods to obtain optimal thresholding in order to obtain ideal denoising. The wavelet filter 174 may include implementation of a discrete wave transform. Alternatively, the wavelet filter 174 may include implementation of a continuous wavelet transform. Parameters associated with the continuous wavelet transform may be adjusted either automatically or manually.

Finally, the preprocessor may calculate the first and second derivative corresponding to the digital data obtained from each ECG lead. This information is beneficial, since these derivatives are related to voltage conduction velocity and turbulence. These processes are known to be associated with the occurrence of SCD.

2.3.2 Isolator Processor

Figure 8:
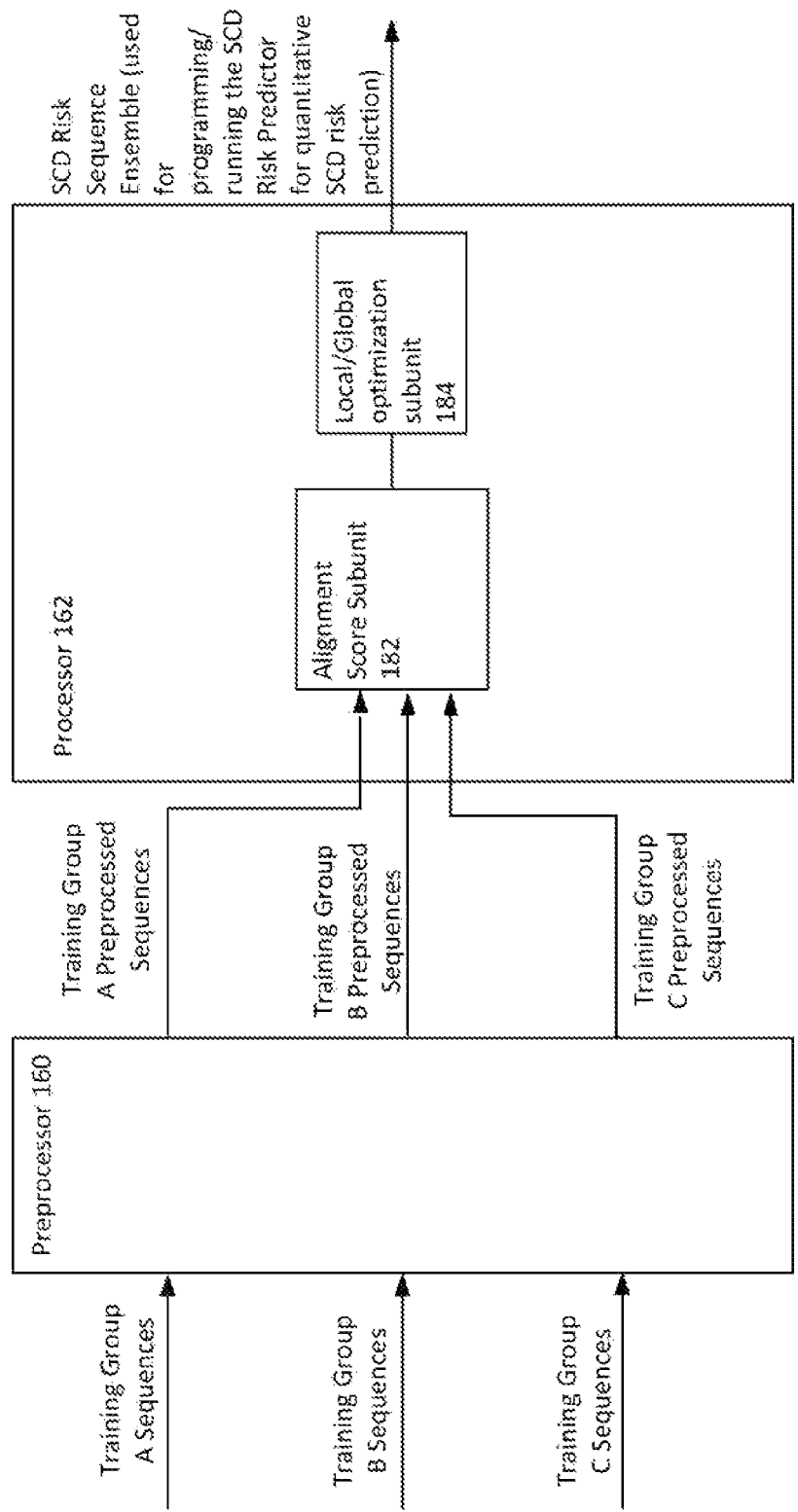
FIG. 8 is a block diagram of the processor of the SCD risk sequences isolator.

The Isolator Processor (represented schematically in FIG. 8) receives as input the output of the Preprocessor 160. The Preprocessor exhaustively determines the alignment scores between all preprocessed ECG sequences from all members of each of the three patient groups. The alignment score—a measurement of the degree of similarity between two sequences or subsequences—is determined by a process or processing component (e.g., alignment Score Subunit 182) of the Isolator Processor. For example, the quantitative measure of sequence alignment may be determined by implementing a modified, scaled Minkowski metric.

The Isolator uses these alignment scores to isolate those sequences present uniquely (relative to Patient Group A) and/or relatively uniquely (relative to Patient Group B) in the ECG sequences of Patient Group C. This process of isolation removes from the ECG sequences of Patient Group C those subsequences present in this patient group responsible for normal (Patient Group A) as well as non-SCD related ECG conduction sequences (present in Patient Group B—those individuals with a variety of non-SCD related conduction defects arising from a multitude of cardiac diseases, e.g., ischemic and non-ischemic). These isolated sequences, as a result of their method of isolation, correlate with SCD risk. These sequences are, by definition, SCD risk sequences.

Figure 9:
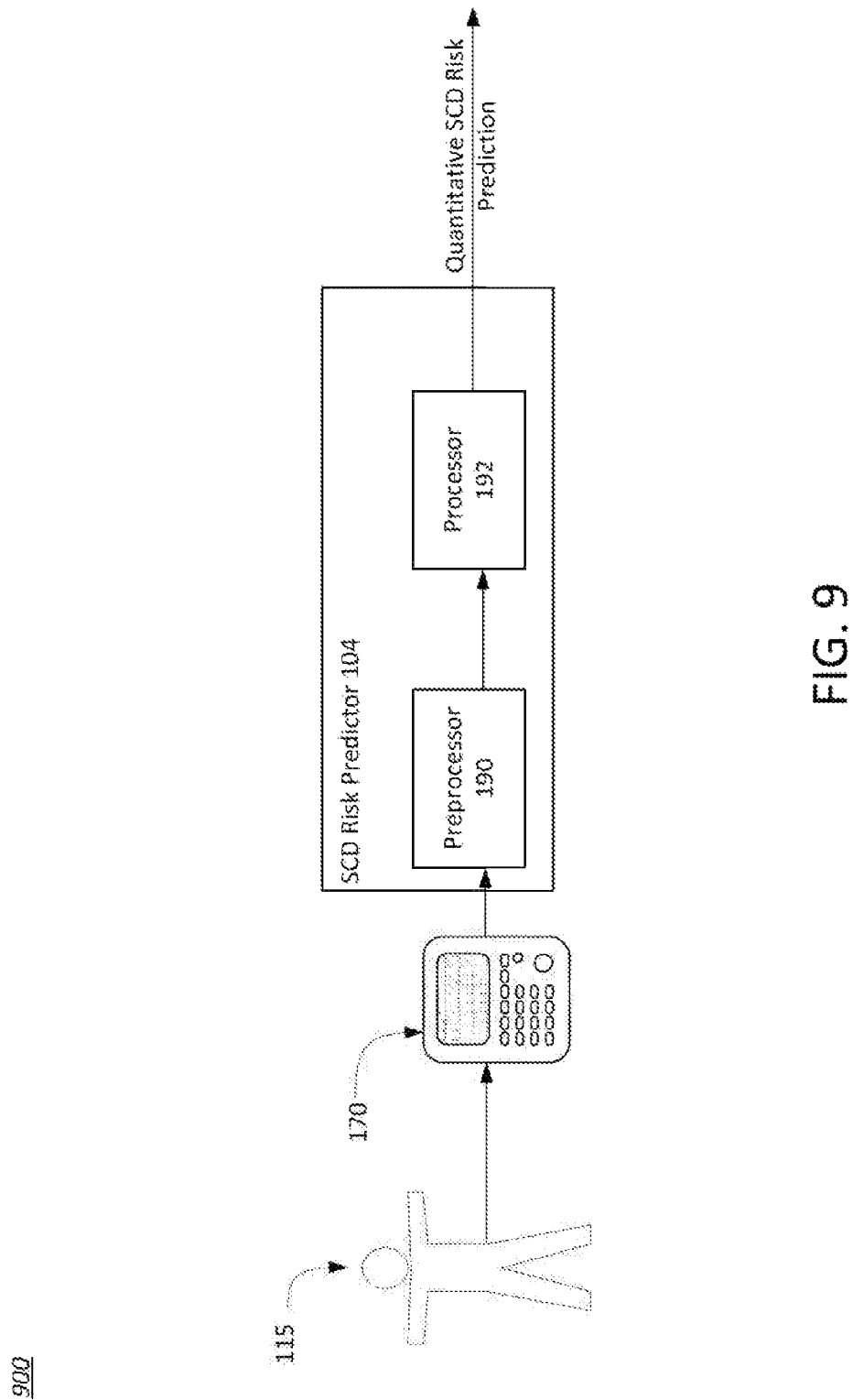
FIG. 9 is a block diagram of the SCD risk predictor and its implementation.

The selection of the particular group of SCD risk sequences used to quantitatively identify individuals at risk for SCD with greatest sensitivity and specificity (e.g., >90%) is determined and constructed using local and global optimization methods such as in an optimization process or processing component (e.g., Local/Global optimization subunit 184). For example, the optimization methods implemented may include one or more of genetic, multi-objective, and annealing optimization techniques. This optimized SCD risk sequence ensemble is the output of the SCD risk sequence Isolator. This sequence ensemble is used to preprogram the SCD risk Predictor (FIG. 9).

3. SCD Risk Predictor

The function of the SCD risk predictor 104 is to quantitatively determine the risk in any given individual of the occurrence of SCD. The SCD risk predictor 104 is preprogrammed (with the optimized SCD risk sequence ensemble) by the SCD risk sequence isolator. Once preprogrammed, the SCD risk predictor is fully functional and able to determine the SCD risk of any individual in a clinical setting. The SCD risk predictor may use as input the digital ECG data obtained from any standard, resting 12-lead ECG device.

The SCD risk predictor 104 functions by determining the alignment (similarity) scores obtained by aligning the test patient digital ECG data to the optimized SCD risk sequence ensembles. The actual SCD risk is quantitatively determined from the number of SCD risk sequences present in the test patient, and by the corresponding alignment scores.

As illustrated in FIG. 9, the predictor 104 may include a preprocessor 190 identical to the preprocessor 160 of the SCD risk sequence isolator 102. The preprocessor 190 may receive as input the 12-lead resting digital ECG data obtained from any individual for whom the calculation of SCD risk is desired. This preprocessor 190 denoises and calculus-transforms the individual's input digital ECG data. (This is identical to the operation of the SCD risk sequence isolator 102.)

With continued reference to FIG. 9, in a manner analogous to the operation of the SCD risk sequence isolator's processor 160, the processor 192 of the SCD risk predictor 104 determines the alignment score for every SCD risk sequence with its corresponding digital ECG sequence (of the same lead and calculus transform) of the digital ECG data of the individual being tested.

Based upon the number of risk sequences present in the test patient and the alignment score determined for each SCD risk sequence, the relative risk of the study patient for experiencing SCD is quantitatively determined.

Finally, the SCD risk predictor may graphically demonstrate the location (and corresponding alignment score) of any and all SCD risk sequences present within the digital ECG of the test individual.

For example, the Predictor may be configured with a processor to calculate an individual's SCD risk score by determining the alignment score between each SCD risk sequence in the risk sequence ensemble stored in its memory (and obtained previously from the Isolator) and the ECG sequences present in the individual being tested.

In some cases, the output of the predictor may be a number ranging from zero to one. In such an example, SCD risk scores correlate with SCD risk as follows:

| SCD RISK SCORE | SCD RISK |
|---|---|
| 0.00-0.10 | very low risk |
| 0.11-0.40 | low risk |
| 0.41-0.70 | moderate risk |
| 0.71-1.00 | high risk |

Although the output may be a real number, in some versions an index may be implemented on a suitable scale for a similar stratification of the risk. Similarly, the output may include a message such as text identifying the nature of the risk (e.g., very low, low, moderate, high etc.). Other formats for stratification may optionally be implemented.

4. Other Implementations

The implementations of each of the isolator 102 and predictor 104 including the processes, parts, units and sub-units thereof are merely illustrative, and not meant to be limiting. Each apparatus may include other parts, units, subunits, or variations thereof. For instance, each of the SCD risk sequence isolator 102 and the SCD risk predictor 104 may be divided into additional parts, units, or subunits.

According to some aspects of the technology, the predictor 104, alone or in combination with other subunits, may be a plug-in application to a standard ECG device, such as a standard resting 12-lead ECG. The SCD risk sequences may be pre-stored in the predictor 104. Moreover, the processes and methods described herein may be performed in whole or in part by a computer or other processing apparatus that may include integrated chips, a memory and/or other control instruction, data or information storage medium. For example, programmed instructions encompassing such methodologies may be coded on integrated chips in the memory of the device. Such instructions may also or alternatively be loaded as software or firmware using an appropriate data storage medium. With such an apparatus, the device can determine and analyze digital ECG sequences from previously measured and received digital ECG data, such as data measured by a discrete measuring device.

In some cases, the predictor may be part of an ATP-ICD (anti-tachycardia pacing (ATP) ICD). In some cases, a predictor may be coupled to a defibrillator, e.g., by wireless communication, so as to receive EGM data for testing purposes. Thus, while a 12-lead ECG has previously been described, the predictor and/or isolator may be configured to operate on 3-lead EGM signals or any other number of leads or electrode measurements.

The SCD risk sequence ensemble may be constructed by an SCD risk sequence isolator similar to the one described in detail herein, but using digital EGM data rather than digital ECG data as input. This would result in the creation of an EGM-specific SCD risk sequence ensemble. This ensemble could then be used to train an appropriate SCD risk predictor unit. Such an SCD risk predictor could be incorporated into an ATP-ICD device to enable anti-tachycardia pacing (ATP) prior to the onset of SCD (SCA), thereby preventing any occurrence of ventricular tachycardia are ventricular fibrillation.

In addition, the SCD risk predictor, which functions in real time, could be used to guide ventricular ablation procedures. The predictor could determine at the time of an ablation procedure (ventricular ablation performed to lower the incidence of SCD in patients at risk for SCD) whether the patient risk for SCD has been successfully reduced and the procedure can be ended. At present, electrical inducibility of ventricular tachycardia is the method used to predict the success of ventricular ablation. This technique has not been demonstrated to be a good predictor of SCD.

5. Some Potential Advantages of the Present Technology

The present technology for identifying SCD risk sequences and predicting and quantifying an individual's risk for SCD has many advantages.

First, the present technology may provide noninvasive risk stratification in individuals. There is, at present, no invasive or noninvasive method for quantifying SCD risk.

Second, the device may identify and isolate critical information hidden within complex data outputs/collections. It may identify and isolate digital electrocardiogram sequences responsible or otherwise associated with the onset of Sudden Cardiac Death (such as those measured within a resting, multi-lead digital ECG).

Third, the present technology may perform risk-stratification in individuals of all risk levels, including no risk, low risk, intermediate risk and high risk. In particular, the present technology may identify individuals at risk for SCD that are not detectable by prior known techniques.

Fourth, the present technology may identify individuals at risk for SCD with high specificity and sensitivity levels not achieved before.

Fifth, the present technology may do so without use of known factors—alone or in combination—presently used in SCD risk-stratification, including left ventricular ejection fraction (LVEF), signal-averaged electrocardiogram (SAECG), microvolt T-wave alternans (MTWA), ambulatory ECG monitoring, heart failure, metabolic factors and autonomic control. As such, the present technology obviates the shortcomings of these technologies as discussed in the background section, although in some embodiments the assessment may be combined with known methods.

Sixth, by identifying individuals at risk for SCD, the present technology has a transformational impact in the initiation of appropriate treatment of SCD (e.g., ICD implantation) and thereby may greatly reduce the incidence of SCD.

Seventh, the present technology poses no risk to any individual, other than the insignificant risk of undergoing a standard ECG.

Eighth, the present technology may successfully calculate SCD risk in all individuals, regardless of whether the individuals have experienced cardiac surgery, and regardless of their clinical history, including history of myocardial infarction, atherosclerotic heart disease, cardiomyopathy, cardiac rhythm, and cardiac condition abnormalities. For example, unlike most of the presently available risk-stratification technologies, the technology described herein can be performed and used to determine SCD risk in individuals with common cardiac rhythm disorders, including atrial fibrillation, premature ventricular contractions (PVCs), as well as bundle branch blocks and complete heart block.

Ninth, the present technology may be used in individuals with no known risk factors for SCD. This includes athletes at the middle school, high school, college and professional level, relatives of individuals who have experienced SCD as well as part of any individuals undergoing a routine physical exam.

Tenth, the present technology may be used to follow the progression of SCD risk in any individual.

Finally, the general principles used in the technology described herein may be used to extract important parameters and information from a vast variety of signals, including speech, sound, graphic, visual, mechanical, and electrical devices.

7. Conclusion

Although aspects of the disclosure herein have been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

The invention claimed is:

1. A method for determining an individual's risk for sudden cardiac death (SCD), the method comprising:
receiving a digital electrocardiogram (ECG) measurement taken from the individual; and
quantitatively determining, in a processor, in the received ECG measurement, presences of predetermined digital electrocardiogram (ECG) sequences indicative of a risk for SCD, wherein the processor assesses quality of alignment between (a) the predetermined digital ECG sequences and derivatives of the predetermined ECG sequences and (b) ECG sequences measured from the individual, and derivatives of the ECG sequences measured from the individual.

2. The method of claim 1, wherein the processor detects presence of a first predetermined ECG sequence of the predetermined ECG sequences by computing an alignment error score related to the first predetermined ECG sequence.

3. The method of claim 2, wherein the ECG measurement is obtained from a standard resting multi-lead ECG machine.

4. The method of claim 3, wherein the processor detects, in the received ECG measurement, the first predetermined digital ECG sequence indicative of the risk for SCD by:
receiving the first predetermined digital ECG sequence indicative of the risk for SCD;
aligning the first predetermined digital ECG sequence with respect to an ECG sequence obtained from the received ECG measurement, to obtain an alignment;
determining an error score for the alignment; and
determining, in the received ECG measurement, presence of the first predetermined digital ECG sequence indicative of the risk for SCD based on the error score.

5. The method of claim 3, further comprising preprocessing, with a preprocessor, the ECG measurement taken from the individual to obtain first and second derivatives of digital ECG data from the ECG measurement.

6. The method of claim 5, wherein the preprocessor preprocesses the digital ECG measurement taken from the individual by:
denoising the digital ECG data, and
deriving first and second derivatives from the denoised digital ECG data.

7. The method of claim 6, wherein the ECG measurement is denoised by at least one of a Finite Impulse Response (FIR) filter and a wavelet packet operation using entropy calculations to optimize threshold settings.

8. The method of claim 7, wherein the noise includes at least one of electrical noise, mechanical noise, respiratory artifacts, white noise, movement artifact, and baseline drift.

9. The method of claim 7, wherein the processor detects, in the received digital ECG measurement, the predetermined digital ECG sequences indicative of the risk for SCD by:
receiving the predetermined digital ECG sequences indicative of the risk for SCD;
aligning ECG sequences from the digital ECG measurement with the predetermined digital ECG sequences associated with SCD risk, to obtain an alignment; and
determining an error score for the alignment; and
determining, in the received digital ECG measurement, the presence of the first predetermined digital ECG sequence indicative of the risk for SCD based upon the error score.

10. An apparatus comprised of:
a storage device containing an optimized ensemble of sudden cardiac death (SCD) risk sequences, wherein SCD risk sequences are determined by assessing quality of alignment of ECG sequences and derivatives of the ECG sequences between multiple individuals.

11. The apparatus of claim 10, further comprising one or more processors, wherein digital ECG measurements of a test patient are preprocessed to:
denoise the ECG measurements to obtain denoised digital ECG data, and derive first and second derivatives of the denoised digital ECG data.

12. The apparatus of claim 11, further comprising at least one of a Finite Impulse Response (FIR) digital filter and a wavelet packet denoising process whose threshold settings are optimally determined by entropy calculations.

13. The apparatus of claim 12, wherein removed noise includes at least one of electrical noise, mechanical noise, respiration artifacts, white noise, movement artifact, and baseline drift.

14. The apparatus of claim 12, wherein the digital ECG measurement from the test patient is obtained from a standard resting multi-lead ECG machine.

15. The apparatus of claim 12, wherein a processor of the one or more processors is configured to align the denoised digital ECG data from the test individual with the optimized ensemble of SCD risk sequences.

16. An apparatus for determining an individual's risk for sudden cardiac death (SCD), the apparatus comprising:
a storage device storing an SCD risk sequence ensemble, wherein SCD risk sequences of the ensemble are determined by assessing quality of alignment of ECG sequences and derivatives of the ECG sequences between multiple individuals; and
a processor in communication with the storage device configured to:
receive a digital ECG measurement taken from a test individual;
detect in the test patient digital ECG measurement any predetermined electrocardiogram (ECG) sequences indicative of a risk for SCD based on the SCD risk sequences in the SCD risk sequence ensemble; and determine quantitative risk for the occurrence of SCD in the individual based on the detection of the predetermined ECG sequences and their alignment.

* * * * *